United States Patent [19]  [11] 3,940,487
La Croix et al.  [45] Feb. 24, 1976

[54] INSECTICIDE COMPOSITIONS COMPRISING A CARBAMATE AND A METHYLENEDIOXYPHENYL COMPOUND

[75] Inventors: Eric Arthur Stuart La Croix, Dorking; Solomon Ezekiel Mhasalker, Worcester Park, both of England

[73] Assignee: Beecham Group Limited, Brentford, England

[22] Filed: Aug. 28, 1973

[21] Appl. No.: 392,301

[30] Foreign Application Priority Data
Sept. 13, 1972 United Kingdom............... 42434/72

[52] U.S. Cl. ............. 424/282; 424/300; 260/340.5
[51] Int. Cl.² ....................................... A01N 9/28
[58] Field of Search .......... 260/340.5; 424/282, 300

[56] References Cited
UNITED STATES PATENTS
2,452,188   10/1948   Hendenburg ...................... 424/282

FOREIGN PATENTS OR APPLICATIONS
698,406   11/1964   Canada ............................... 424/282

Primary Examiner—V. D. Turner

[57] ABSTRACT

Insecticidal compositions are described containing new insecticidal compounds. The insecticidal activity of certain carbamates is enhanced by addition of a compound derived from methylenedioxybenzene or ethylenedioxybenzene. The insecticidal compositions have an acceptable carrier which does not damage animals or plants or the locus to which they are applied or the life forms inhabiting the locus. The compositions are applied as sprays, aerosols or in other forms.

8 Claims, No Drawings

INSECTICIDE COMPOSITIONS COMPRISING A CARBAMATE AND A METHYLENEDIOXYPHENYL COMPOUND

This invention relates to insecticidal compositions and to certain novel insecticidal compounds and their manufacture.

Carbamates, that is compounds containing the -O.-CO.N< groups, are known to have insecticidal activity.

Many carbamate insecticides have the advantages of not containing organic phosphorus or chlorine or similar environmentally disadvantageous groups. Unfortunately it is frequently the case that their action is not as great as the organophosphorus and halogen containing insecticides so that a greater amount is sometimes required before achieving the same effect.

We have now found that the insecticidal activity of certain carbamates may be enhanced to a surprising extent by the addition of a further compound derived from methylenedioxybenzene or ethylenedioxybenzene.

Accordingly, the present invention provides an insecticidal composition comprising (a) 20 parts of a compound of formula (I):

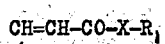

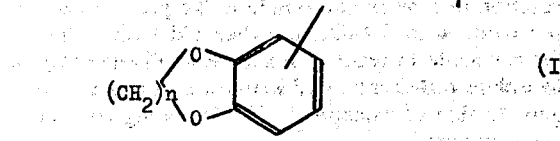

wherein $n$ is 1 or 2, X is an oxygen atom or a bond joining the moiety $R_1$ to the carbonyl group, and $R_1$ is a hydrocarbon group of 1–12 carbon atoms; (b) from 1 to 400 parts of a compound of the formula (II):

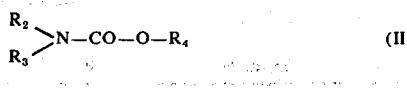

wherein $R_2$ is a hydrogen atom or a lower alkyl group optionally substituted by a halogen atom, $R_3$ is a lower alkyl group optionally substituted by a halogen atom and $R_4$ is an optionally substituted aromatic or heteroaromatic group; and (c) an acceptable carrier An "acceptable carrier" is one that allows the distribution of the mixed insecticides over the required locus without causing unacceptable damage to that locus or to desirable life forms which may inhabit that locus. For example, if the composition is to be applied to an animal such as a sheep, the carrier must not adversely effect the sheep or its handlers; or if the composition is applied to plants, then the carrier must not be phytotoxic.

Suitable values of $R_1$ for compounds of formula (I) include aliphatic, alicyclic, aromatic, or araliphatic hydrocarbon groups such as straight or branched groups of 1–12 carbon atoms, which may contain 1, 2, 3 or more degrees of unsaturation, araliphatic groups such as benzyl, phenylethyl and the like, or cyclic systems such as alicyclic rings of 3 to 6 carbon atoms.

Preferred groups $R_1$ are lower aliphatic groups such as the methyl, ethyl, n-propyl, n-butyl, iso-butyl, sec-butyl, t-butyl, 2-methyl-prop-1-enyl, 1,2-dimethylbutyl, cyclohexylmethyl and like groups. The term "lower" when used herein means that the group contains from 1 to 8 carbon atoms.

In compounds of formula (I), $n$ is preferably 1 and X is a bond.

An especially preferred sub-group of formula (I) to be present in the insecticidal composition are those of formula (III):

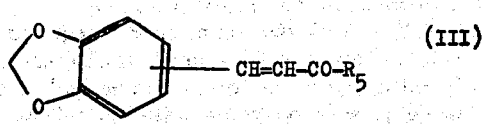

wherein $R_5$ is a lower alkyl group.

Suitable values for $R_2$ include the hydrogen atom and the methyl, chloromethyl and ethyl groups.

Suitable values for $R_3$ include the methyl, chloromethyl, ethyl, propyl, hexyl and octyl groups. Preferably the group $-NR_2R_3$ is the $-NHCH_3$, $N(CH_3)_2$ or $-NHCH_2Cl$ group.

Suitable groups $R_4$ include the phenyl, naphthyl and imidazole groups each of which may be substituted by a lower aliphatic hydrocarbon group, and/or a methoxyl group, or by 2 t-butyl groups 1 methoxyl and 1 propenyl group or by 2 methyl groups and 1 propyl group.

Preferred groups $R_4$ include the 1-naphthyl, 3,5-di-t-butyl phenyl, 2-methoxyl-4(2-propenyl)phenyl and 1-(4,5-dimethyl-2-propylimidazole) groups.

Especially preferred compounds of formula (II) include 1-naphthyl-N-methyl carbamate, 3,5-di-t-butylphenyl-N-methyl carbamate, 1-(2-methoxyl-4-prop-2-en)phenyl-N-methyl carbamate and 4,5-dimethyl-2-propylimidazole-1-N,N-dimethyl carbamate.

The method of application of a composition of the invention should be chosen to suit the nature of the insect or its environment and may include those listed below. The nature of the composition which is used will also depend upon the factors which determine the method of administration.

Thus the active ingredient may be administered as a spray composition prepared by the dilution of emulsifiable concentrated solutions in solvents, for example, hydrocarbon solvents such as petroleum fractions, xylene and toluene; from emulsion concentrates; or from wettable dispersable powders which are diluted with water. The compositions in these cases will include suitable wetting, dispersing or emulsifying agents well known in the art.

Alternatively the active ingredients may be incorporated into powders with a solid carrier for direct application. Oily compositions for spraying without dilution may also be used.

The active ingredient may also be used as a concentrate for addition to dips or sprays or in the form of aerosol preparations for domestic, horticultural and veterinary use.

Where the insects are associated with animals, the active ingredient may be presented as a solution or emulsion for topical application to the animal. The present invention finds particular use in the control of blowfly on sheep for which purpose it is conveniently applied topically as a dip, jet or a spray. If the active ingredient is used systemically, then any preparations suitable for dermal application may be used, since the active ingredient is capable of penetrating through the skin of the animal resulting in insecticidal levels in the blood. Aqueous emulsions or alcoholic solutions of the active ingredient are suitable for dermal application. The active ingredient may also be presented orally in the form of a drench, i.e., an aqueous suspension or solution given by mouth.

The composition may include other insecticidal agents and/or plant fungicides in addition to the active ingredients of the present invention.

If the insecticidal composition is required for household use, for example, against Masca domestica, it may be presented in the form of an aerosol or an impregnated plastics body for sustained release or similar conventional presentation.

Certain of the compounds of formula (I) are novel. Thus in a second aspect the invention provides compounds of the formula (IV):

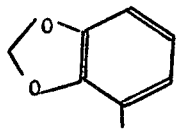

CH=CH-CO-R$_6$ (IV)

wherein R$_6$ is a hydrocarbon group of 1–12 carbon atoms.

Preferred compounds of formula (IV) include those wherein R is a lower alkyl group.

Compounds of the formula (IV) may be prepared by the base catalysed condensation of 2,3-methylenedioxybenzaldehyde and a ketone of formula (V):

R$_6$— CO— CH$_3$  (V)

wherein R$_6$ has the same meaning as given above.

This reaction may be carried out in an aqueous ethanolic solution of the presence of a strong base such as sodium hydroxide under those conditions, commonly used to bring about such reactions.

The following examples serve to illustrate the invention. Where no melting points are given IR, UV, NMR and microanalysis were consistent to the structure.

EXAMPLE 1

3,4-Methylenedioxybenzylidine ter-butyl ketone- Ethanol (80 ml) was placed in a 250 ml conical flask equipped with a stirrer and dropping funnel. ter-Butyl methyl ketone (10 g; 0.1 mole) and piperonal (15 g; 0.1 mole) were added and stirring started. Sodium hydroxide (4 g; 0.1 mole) was dissolved in 40 ml of water and added dropwise to the above stirred mixture for 5–10 minutes. The reaction mixture was further stirred for ca. 60 hours at room temperature. The precipitated solid was filtered, washed with water and dried. The solid was then recrystallized from n-hexane to give pale yellow needles, having a melting point 93°–94°C (reported m.p. 95°C). Yield obtained was 22.2 g. This is equivalent to a yield of 94–95% of the theoretical.

EXAMPLES 2 – 23

The following compounds of the formula

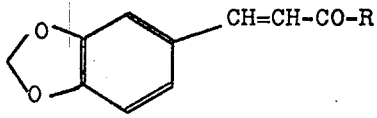

were prepared in a manner analogous to that of Example 1:

| EXAMPLE | R | m.p. °C |
|---|---|---|
| 2 | —CH$_3$ |  |
| 3 | —CH$_2$CH$_3$ |  |
| 4 | —(CH$_2$)$_2$CH$_3$ | 56 |
| 5 | —CH(CH$_3$)$_2$ | 57 |
| 6 | Cyclopropyl | 80 |
| 7 | —(CH$_2$)$_3$CH$_3$ | 73 |
| 8 | —CH$_2$CH(CH$_3$)$_2$ | 68 |
| 9 | —CH(CH$_3$)CH$_2$CH$_3$ | 35 |
| 10 | —(CH$_2$)$_4$CH$_3$ | 61 |
| 11 | —CH$_2$CH$_2$CH(CH$_3$)$_2$ |  |
| 12 | —(CH$_2$)$_5$CH$_3$ | 59 |
| 13 | —(CH$_2$)$_6$CH$_3$ | 52 |
| 14 | —(CH$_2$)$_7$CH$_3$ | 57 |
| 15 | —(CH$_2$)$_8$CH$_3$ | 60 |
| 16 | —(CH$_2$)$_9$CH$_3$ | 64 |
| 17 | —CH=C(CH$_3$)$_2$ |  |
| 18 | —CH$_2$CH$_2$CH=C(CH$_3$)$_2$ | 60 |
| 19 | —CH$_2$C(CH$_3$)$_3$ | 59 |
| 20 | —CH(CH$_3$)CH$_2$CH$_2$CH$_3$ | bpt 120°/ 0.3 mm |
| 21 | —CH(CH)$_3$CH(CH$_3$)C$_2$H$_5$ |  |
| 22 | —CH$_2$C$_6$H$_5$ |  |
| 23 | —CH$_2$Cyclo C$_6$H$_{11}$ | 96–8 |

EXAMPLES 24–28

3,4-Ethylenedioxybenzaldehyde was prepared by the reaction of ethylenedibromide in the presence of copper oxide with 3,4-dihydroxybenzaldehyde. This was further made to react with ketone in alkaline medium to isolate α,β-unsaturated ketones in a manner analogous to that of example 1. The following compounds were prepared.

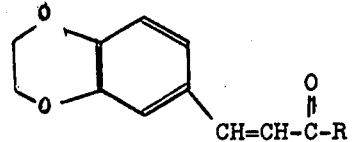

CH=CH-C-R

| Example | R |
|---|---|
| 24 | Cyclopropyl |
| 25 | —CH$_2$(CH$_2$)$_2$CH$_3$ |
| 26 | —CH$_2$CH(CH$_3$)$_2$ |
| 27 | —C(CH$_3$)$_3$ |
| 28 | —CH$_2$—C(CH$_3$)$_3$ |

EXAMPLES 29–46

A method analogous to that of example 1 was used to prepare the following compounds:

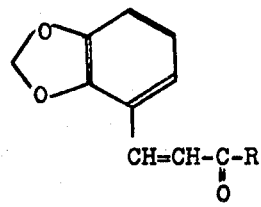

CH=CH-C-R
         ‖
         O

| Example | R | B.P. °C/m |
|---|---|---|
| 29 | —CH$_3$ | — |
| 30 | —CH$_2$CH$_3$ | — |
| 31 | —(CH$_2$)$_2$CH$_3$ | 164/0.2 |

-continued

| Example | R | B.P. °C/m |
|---|---|---|
| 32 | —CH(CH$_3$)$_2$ | — |
| 33 | —Cyclopropyl | — |
| 34 | —(CH$_2$)$_3$CH$_3$ | 145–6/0.4 |
| 35 | —CH$_2$CH(CH$_3$)$_2$ | 176/0.2 |
| 36 | —CH(CH$_3$) CH$_2$CH$_3$ | 168/0.2 |
| 37 | —C(CH$_3$)$_3$ | M.P.71° |
| 38 | —(CH$_2$)$_4$CH$_3$ | 170/0.2 |
| 39 | —(CH$_2$)$_2$CH(CH$_3$)$_2$ | 183/0.2 |
| 40 | —(CH$_2$)$_5$CH$_3$ | — |
| 41 | —(CH$_2$)$_6$CH$_3$ | — |
| 42 | —(CH$_2$)$_7$CH$_3$ | 180/0.2 |
| 43 | —(CH$_2$)$_8$CH$_3$ | — |
| 44 | —(CH$_2$)$_9$CH$_3$ | — |
| 45 | —CH$_2$—C(CH$_3$)$_2$CH$_3$ | — |
| 46 | —CH$_2$—cyclohexyl | 194/0.2 |

EXAMPLES 47–51

The following 3,4-Methylenedioxycinnamic acid esters were prepared by known methods:

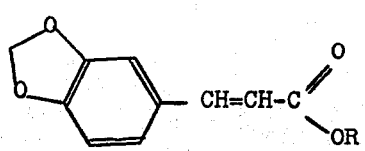

| Example | R |
|---|---|
| 47 | —CH$_3$ |
| 48 | —CH$_2$CH$_3$ |
| 49 | —CH$_2$CH$_2$CH$_3$ |
| 50 | —CH$_2$(CH$_2$)$_2$CH$_3$ |
| 51 | —CH$_2$—CH(CH$_3$)$_2$ |

EXAMPLE 52

Synergistic activities of 2,3- and 3,4-Methylene dioxyphenyl series.

The synergistic activity of the materials was tested by dissolving equal weights of the material and carbaryl in acetone, placing sufficient volume of the mixture to give the required weight of materials per sq. cm. of surface in glass Petri dishes and then evaporating to dryness in a stream of cold air. Twenty-five 4-day old *Drosophila melanogaster* adults were then confined in each dish, with a supply of 10% sucrose in water, for 24 hours, at the end of which time the number of dead flies was counted. First tests were carried out at a concentration of 1.0 $\mu$g/cm$^2$; if a 100% mortality was obtained, tests were carried out to determine the LD$_{50}$ of the mixture.

In the table below, the LD$_{50}$ is expressed as the concentration of each material (synergist and carbaryl) in terms of $\mu$g/cm$^2$. (Carbaryl is 1-naphthyl-N-methyl carbamate)

Carbaryl by itself at 10$\mu$g/cm$^2$ caused no deaths.

| COMPOUND OF EXAMPLE NO. | LD$_{50}$ (in $\mu$g/cm$^2$ of synergist and carbaryl) |
|---|---|
| 1 | 0.02 |
| 3 | 0.2 |
| 4 | 0.15 |
| 7 | 0.5 |
| 8 | 0.1 |
| 9 | 0.09 |
| 17 | 0.28 |
| 19 | 0.5 |
| 20 | 0.13 |
| 21 | 0.05 |
| 23 | 0.6 |
| 31 | 0.2 |
| 32 | 0.4 |
| 34 | 0.1 |
| 35 | 0.06 |
| 36 | 0.09 |
| 37 | 0.08 |
| 38 | 0.1 |
| 39 | 0.09 |
| 45 | 0.06 |
| 47 | 0.8 |
| 48 | 0.08 |
| 49 | 0.04 |
| 50 | 0.05 |
| 51 | 0.09 |

EXAMPLE 53

Using the test method of example 37 the following results were obtained.

| COMPOUNDS UNDER TEST | LD$_{50}$ ($\mu$g/cm$^2$) |
|---|---|
| X | 2.3 |
| X + Example 27 | 0.07 |
| Y | 0.9 |
| Y + Example 27 | 0.6 |

X is 1-(2-methoxy-4-prop-2-en-phenyl)-N-methyl carbamate. Y is 1-(4,5-dimethyl-2-propylimidazole)-N,N$^1$-dimethyl carbamate.

EXAMPLE 54

Four-day old susceptible *Musca domestica* (housefly) adults were anaesthetized in CO$_2$, 20 males being placed in one dish and 20 females being placed in another dish, of two glass vessels and then dosed topically with a 1:1 mixture of the synergist/insecticide in acetone from a micro-pipette applicator. The flies were confined with sugar and water for 24 hours, when the number of deaths was recorded.

In the table below, the LD$_{50}$ is expressed as the concentration of each material (synergist and insecticide) in terms of $\mu$g/fly.

| COMPOUND | LD$_{50}$($\mu$g/fly) of synergist and insecticide | |
|---|---|---|
| | Males | Females |
| Carbaryl | >10 | >10 |
| Carbaryl + Example 9 | 0.5 | 1.0 |
| Carbaryl + Example 17 | 0.25 | 0.95 |
| Carbaryl + Example 21 | 0.3 | 0.7 |
| Carbaryl + Example 27 | 0.2 | 0.32 |
| Carbaryl + Example 50 | 0.3 | 0.8 |
| Carbaryl + Example 51 | 0.5 | 1.1 |
| X | 1.1 | 2.0 |
| X + Example 27 | 0.3 | 0.5 |
| Y | 7.0 | 15.0 |
| Y + Example 27 | 3.0 | 5.0 |

EXAMPLE 55

Synergistic activity with larvae of sheep blowflies was tested as follows.

0.5 ml of a 1000 ppm solution in acetone (equal weights of synergist and insecticide) was absorbed onto a strip of paper tissue and the acetone was then evaporated off. The tissue was then placed in a 75 × 19 mm glass tube, 0.5 ml of calf serum was added, 25, 12-hour old first instar larvae were placed on each tissue, and the tube was sealed with a "Tricel" cover. After 48 hours, the number of dead larvae in each tube were counted.

The synergists caused no deaths when tested by themselves.

In the table below, the $LD_{50}$ is expressed as the concentration of each material (synergist + insecticide) in terms of parts per million (ppm).

| COMPOUND | $LD_{50}$ (ppm) | |
| --- | --- | --- |
| | (a) Susceptible *Lucilia sericata* larvae | (b) Resistant *Lucilia cuprina* larvae (strain RD) |
| Z | 1.6–1.8 | 15–21 |
| Z + Example 1 | | 3–4 |
| X | 9–11 | 26–28 |
| X + Example 1 | 2–4 | 8 |
| Y | 310 | 660 |
| Y + Example 1 | 180 | 250 |

Z is 3,5-di-t-butylphenyl-N-methyl carbamate.

What we claim is:

1. An insecticidal composition comprising equal parts of (a) a compound of formula (I):

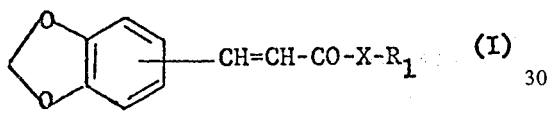 (I)

wherein X is an oxygen atom or a bond joining $R_1$ to the carbonyl group and $R_1$ is alkyl of 1 to 12 carbon atoms or alkenyl of up to 12 carbon atoms; and (b) 1-naphthyl-N-methyl carbamate; 1-(2-methoxy-4-prop-2-en)-phenyl-N-methyl carbamate; or 3,5-di-t-butyl-phenyl-N-methyl carbamate; in combination with an insecticidally acceptable carrier.

2. A composition according to claim 1 wherein X is a bond and $R_1$ is alkyl of 1–8 carbon atoms.

3. A composition according to claim 1 wherein $R_1$ is methyl, ethyl, n-propyl, n-butyl, iso-butyl, sec.-butyl, t-butyl, 2-methylprop-1-enyl, 1,2-dimethylbutyl or cyclohexylmethyl.

4. A composition according to claim 1 wherein the compound of (a) is 3,4-methylenedioxybenzylidine terbutyl ketone, and the compound of (b) is 1-naphthyl-N-methyl carbamate.

5. A composition according to claim 1 wherein the compound of (a) is 3,4-methylenedioxybenzylidine terbutyl ketone, and the compound of (b) is 1-(2-methoxy-4-prop-2-en)phenyl-N-methyl carbamate.

6. A composition according to claim 1 wherein the compound of (a) is 3,4-methylenedioxybenzylidine terbutyl ketone, and the compound of (b) is 3,5-di-5-butyl-phenyl-N-methyl carbamate.

7. A composition according to claim 1 wherein the compound of formula (I) is of the formula:

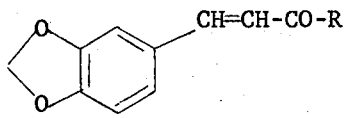

wherein R is alkyl of 1–10 carbon atoms, cyclopropyl, alkenyl of 4–8 carbon atoms or cyclohexylmethyl.

8. An insecticidal composition comprising equal parts of (a) a compound of formula (III):

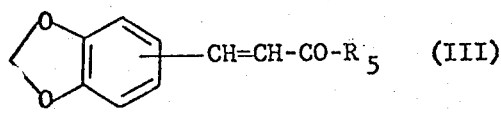 (III)

wherein $R_5$ is alkyl of 1–8 carbon atoms; and (b) 1-naphthyl-N-methyl carbamate, 3,5-di-t-butylphenyl-N-methyl carbamate or 1-(2-methoxy-4-prop-2-en)-phenyl-N-methyl carbamate; in combination with an insecticidally acceptable carrier.

* * * * *